United States Patent
Doguet et al.

(10) Patent No.: US 10,507,330 B2
(45) Date of Patent: Dec. 17, 2019

(54) CENTERING KIT FOR ALIGNING AN EXTERNAL ELEMENT WITH RESPECT TO AN IMPLANTED MEDICAL DEVICE AND CORRESPONDING METHOD

(71) Applicant: SYNERGIA MEDICAL, Mont-Saint-Guibert (BE)

(72) Inventors: Pascal Doguet, Mont-Saint-Guibert (BE); Aurelie De Cock De Rameyen, Mont-Saint-Guibert (BE); Gregory Thiebaut, Mont-Saint-Guibert (BE)

(73) Assignee: Synergia Medical, Mont-Saint-Guibert (BE)

(*) Notice: Subject to any disclaimer, the term of this patent is extended or adjusted under 35 U.S.C. 154(b) by 0 days.

(21) Appl. No.: 16/095,723

(22) PCT Filed: May 24, 2016

(86) PCT No.: PCT/EP2016/061722
§ 371 (c)(1),
(2) Date: Oct. 23, 2018

(87) PCT Pub. No.: WO2017/202455
PCT Pub. Date: Nov. 30, 2017

(65) Prior Publication Data
US 2019/0168004 A1    Jun. 6, 2019

(51) Int. Cl.
*A61N 1/378* (2006.01)
*H02J 50/10* (2016.01)
(Continued)

(52) U.S. Cl.
CPC ............ *A61N 1/3787* (2013.01); *A61B 5/065* (2013.01); *A61N 1/37223* (2013.01);
(Continued)

(58) Field of Classification Search
CPC ........ A61N 1/3787; H02J 50/80; H02J 50/90; H02J 50/10; H02J 50/30; H02J 7/025;
(Continued)

(56) References Cited

U.S. PATENT DOCUMENTS

| 2008/0027293 A1 | 1/2008 | Vodermayer et al. |
| 2010/0217353 A1 | 8/2010 | Forsell |

(Continued)

FOREIGN PATENT DOCUMENTS

| WO | 9811942 A1 | 3/1998 |
| WO | 2005000391 A1 | 1/2005 |

(Continued)

OTHER PUBLICATIONS

International Search Report dated Feb. 20, 2017 for International Application No. PCT/EP2016/061722 filed May 24, 2016.

*Primary Examiner* — Paula J Stice
(74) *Attorney, Agent, or Firm* — Avery N. Goldstein; Blue Filament Law PLLC (57) ABSTRACT

A kit of parts and a system for centering an external element with respect to an implantable medical device is provided that includes: •An implantable medical device (20) for being implanted under the skin of a patient and having an internal housing with a light source (22) positioned such as to emit a light beam coaxial to a secondary axis (Z2), •An external element (10) having —a number, N>2, of photodetectors (12a-12d) forming a polygon of N edges, normal to a primary axis (Z1), and —an indicator (4) indicating how the external element is to be displaced over the the skin to position the external element with the primary axis (Z1), being coaxial with the secondary axis (Z2), as a function of the energy received by each of the N photodetectors. A corresponding method for aligning the external element and the implantable medical device are provided.

17 Claims, 5 Drawing Sheets

(51) Int. Cl.
  *H02J 50/90* (2016.01)
  *H02J 50/30* (2016.01)
  *A61B 5/06* (2006.01)
  *H02J 7/02* (2016.01)
  *H02J 50/80* (2016.01)
  *A61N 1/372* (2006.01)

(52) U.S. Cl.
  CPC .............. *H02J 7/025* (2013.01); *H02J 50/10* (2016.02); *H02J 50/30* (2016.02); *H02J 50/80* (2016.02); *H02J 50/90* (2016.02); *A61B 2560/0219* (2013.01); *A61F 2250/0001* (2013.01); *A61N 1/37229* (2013.01); *A61N 1/37235* (2013.01)

(58) Field of Classification Search
  CPC ............. A61B 5/065; A61B 2560/0219; A61F 2250/0001
  See application file for complete search history.

(56) References Cited

U.S. PATENT DOCUMENTS

| | | |
|---|---|---|
| 2011/0004278 A1 | 1/2011 | Aghassian et al. |
| 2015/0077050 A1 | 3/2015 | Van Funderburk |

FOREIGN PATENT DOCUMENTS

| | | |
|---|---|---|
| WO | 2006012426 A2 | 2/2006 |
| WO | 2010042055 A1 | 4/2010 |
| WO | 2010042056 A1 | 4/2010 |

CENTERING KIT FOR ALIGNING AN EXTERNAL ELEMENT WITH RESPECT TO AN IMPLANTED MEDICAL DEVICE AND CORRESPONDING METHOD

TECHNICAL FIELD

The present invention concerns a system comprising an implantable medical device which, when implanted, must cooperate transcutaneously with an external element. In particular it concerns such system provided with a simple and efficient solution for optimally aligning the external element with the implanted medical device which accurate position is not visible optically when implanted under the skin of a patient, in a position where they can cooperate optimally. A preferred type of cooperation between the external element and an implanted medical device is the exchange of electromagnetic waves between an emitter and a receiver for the wireless transfer of energy or information/instructions.

BACKGROUND OF THE INVENTION

Many types of implantable medical devices exist and have various functions. Once implanted, they must cooperate with an external element to continue their function. For example, a reservoir can be implanted to deliver a liquid composition at a given rate. The reservoir must be refilled at regular intervals, for example by means of a syringe. For implantable medical devices consuming electrical energy and that incorporate a rechargeable battery, such as neurostimulators, their batteries must be replenished at regular intervals. An implantable medical device may collect information from the implantable medical device itself (e.g., battery level of charge, logging information, physiological parameters) and from the subcutaneous environment surrounding it, and this information must be transferred to the exterior. An implantable medical device may need to be programmed or re-programmed after its implantation.

All these operations can easily be performed with an external element providing the type of cooperation required by a specific type of implantable medical device. In most cases, however, an optimal transcutaneous (wireless) cooperation between an implantable medical device and an external element requires an optimal positioning of the external element relative to the implantable medical device. For example, the intensity of an electromagnetic signal emitted by an emitter along a transmission axis drops rapidly with the radial distance from said transmission axis. Typically, a misalignment of the order of the mm may drop the strength of the reception of a signal by several tens of %. Similarly, the internal rechargeable battery of an implantable medical device can be recharged by inducing a current in a secondary coil of the implanted medical device by means of a magnetic field generated by current circulating in a primary coil in an external element. The intensity of the induced current in the secondary coil varies substantially as a function of the position of the primary coil with respect to the secondary coil.

WO2010042055 proposes to provide a system with a wireless feedback system arranged to transmit feedback information from a RFID transmitter. The feedback information thus transmitted is used to optimize the position of the primary coil of a charger relative a secondary coil of an implanted medical device.

WO9811942 describes an alignment circuit and indicator to indicate whether the coils of an external charger and of an implantable medical device are properly aligned. The alignment circuit senses current in the primary coil to determine whether the angular and lateral alignment is optimal by sensing a peak DC current.

WO2006012426 developed a system for locating an implanted object using an external antenna. WO2010042056 uses a system wherein the implanted medical device transmits feedback information to the external charger including the strength of the magnetic field generated by the primary coil.

WO2005000391 describes a sensor circuit arranged close to the primary coil so that a part of the magnetic field from the secondary coil is enclosed by the sensor circuit thereby providing an induction in the sensor circuit which can be detected and thereby indicates the condition in the secondary circuit.

The present invention proposes an original solution for the alignment of an external element relative to an implanted medical device. The system is simple, effective and cost effective. It can also be automated. These and other advantages of the present invention are presented in the next sections.

SUMMARY OF THE INVENTION

The present invention is defined in the appended independent claims. Preferred embodiments are defined in the dependent claims. In particular, the present invention concerns a kit of parts for centring an external element with respect to an implantable medical device, said kit of parts comprising:
(A) An external element comprising an external housing characterized by a primary axis, Z1, and containing an external electronic unit,
(B) An implantable medical device for being implanted under the skin of a patient and comprising an internal housing characterized by a secondary axis, Z2,
Characterized in that,
(C) The implantable medical device further comprises a light source positioned such as to emit a light beam coaxial to the secondary axis, Z2, and of wavelength and intensity sufficient for being transmitted through the tissues and skin separating the implantable medical device from the exterior when implanted under the skin of a patient, and in that,
(D) The external element comprises:
(a) A number, N>2, of photodetectors forming a polygon of N edges, normal to the primary axis, Z1, and which centroid belongs to the primary axis, Z1, and
(b) An indicator indicating how the external element is to be displaced over the surface of the skin of a patient in order to position the external element with the primary axis, Z1, being coaxial with the secondary axis, Z2, of the implantable medical device, as a function of the energy received by each of the N photodetectors from the light beam emitted by the light source.

The present invention is particularly advantageous in systems wherein,
(a) the internal housing of the implantable medical device contains an internal electronic unit comprising an internal energy emitter and/or an internal energy receiver defined by a secondary transmission axis, Y2, and wherein (b) the external electronic unit of the external element comprises an external energy receiver and/or an external energy emitter defined by a primary transmission axis, Y1, and wherein when the internal energy emitter and/or internal energy receiver faces the external energy emitter and/or external energy receiver with the secondary transmission axis, Y2, being coaxial to the primary transmission axis, Y1, the secondary axis, Z2, of the implantable medical device is positioned coaxially to the primary axis, Z1, allowing an optimized energy transfer between the internal energy emitter and/or internal energy receiver of the implantable medical device and the external energy emitter and/or external energy receiver of the external element, and wherein the energy is preferably transferred as an electromagnetic wave. In particular, the electromagnetic wave can be selected among a magnetic link, an optical wave of wavelength comprised between 400 and 1700 nm, preferably between 650 and 1350 nm, a radiowave of frequency comprised between 1 kHz and 2.5 GHz, preferably between 0.1 and 100 MHz, more preferably between 1 and 30 MHz, or a radiowave of frequency comprised between 300 MHz and 2.4 GHz.

In a first embodiment, the kit of parts has a coaxial configuration, wherein

The secondary transmission axis, Y2, of the internal energy emitter and/or internal energy receiver of the implantable medical device is coaxial to the secondary axis, Z2, (Y2=Z2), and The primary transmission axis, Y1, of the external energy receiver and/or external energy emitter of the external element is coaxial to the primary axis, Z1, (Y1=Z1).

In a second embodiment, the kit of parts has an offset configuration, wherein

The secondary transmission axis, Y2, of the internal energy emitter and/or internal energy receiver of the implantable medical device is parallel to and offset from the secondary axis, Z2, by a distance, d, (Y2≠Z2, Y2∥Z2), and The primary transmission axis, Y1, of the external energy receiver and/or external energy emitter of the external element is parallel to and offset from the primary axis, Z1, by the distance, d, (Y1≠Z1, Y1∥Z1), and wherein The external element comprises a pointer pointing the angular position with respect to the primary axis, Z1, required by the external element in order to bring the primary transmission axis, Y1, coaxially to the secondary transmission axis, Y2, when the primary axis, Z1, and secondary axis, Z2, are coaxial.

The kit of parts of the present invention can be applied to an external charger for charging an internal battery of an implanted medical device, in which (A) The external element is an electric charger connectable to a source of electric current for feeding in electric current a primary coil made of one or more wires coiled about the primary axis, Z1, thus forming an external emitter of magnetic waves, and (B) The internal electronic unit of the implantable medical device is fed with electric current by a rechargeable battery coupled to a secondary coil made of one or more wires coiled about the secondary axis, Z2, thus forming an internal receiver, Such that when the electric charger is located adjacent to the implantable medical device with the primary axis, Z1, positioned coaxially to the secondary axis, Z2, and when the primary coil is fed with electric current, a magnetic link is formed and the induction of an electric current in the secondary coil is optimized, which serves to recharge the battery. Because the secondary axis, Z2, passes through a central clearing defined by the secondary coil, which can accommodate a light source, the present application can easily be designed with a coaxial configuration.

In an alternative application, (A) The external element can be a programming unit and the electromagnetic waves emitted by the external emitter are programming instructions, and (B) The internal electronic unit of the implantable medical device is programmable, Such that when the external energy emitter of the programming unit is positioned adjacent to the internal energy receiver of the programmable implantable medical device with the primary and secondary transmission axes, Y1, Y2, positioned coaxially, the programming instructions emitted by the external energy emitter are received optimally by the internal energy receiver and transmitted to the internal electronic unit In yet an alternative application, (A) The external electronic unit of the external element comprises an external receiver allowing the reception of electromagnetic waves propagating in a direction parallel to the primary transmission axis, Y1, (B) The internal electronic unit of the implantable medical device comprises an internal energy emitter configured for emitting electromagnetic waves in a direction parallel to the secondary transmission axis, Y2, Such that when the external energy receiver of the external element is positioned adjacent to the internal energy emitter of the implantable medical device, with the primary and secondary transmission axes, Y1, Y2, positioned coaxially, the electromagnetic wave emitted by the internal energy emitter is received optimally by the external energy receiver. The electromagnetic wave emitted by the internal energy emitter may for example comprise data of the implantable medical device or data collected by the implantable medical device. The light source of the implantable medical device may also act as internal energy emitter for transferring the data of the implantable medical device or collected by the implantable medical device in the form of an optical wave. In this case a coaxial configuration is easily designed.

In order to indicate how the external element must be displaced in order to bring the primary axis, Z1, coaxial to the secondary axis, Z2, a processor or an electronic logic control circuit can be used which is configured for carrying out the following steps:

(a) Measure the energy received by each of the photodetectors of the external element from the light source, (b) Calculate the mean energy, μm, defined as the average of the energies, $E_i$, received by each of the N photodetectors, $E_m = \Sigma E_i / N$, with i=1 to N, (c) For each photodetector, determine whether the received energy, $E_i$, falls within an optimal range comprised between (Em−ε) and (Em+ε), wherein ε is a predefined optimal deviation, (d) If the energy, $E_i$, received by each of the N photodetectors falls within the optimal range, indicate that the external element is optimally positioned with the primary axis, Z1, being coaxial to the secondary axis, Z2, within the optimal deviation, and preferably (e) If the energy, $E_i$, of at least one of the N photodetectors falls out of the optimal range, indicate that the external element is not positioned optimally and indicate the direction the external element must be displaced in order to bring the primary axis, Z1, coaxially to the secondary axis, Z2, of the implantable medical device.

The comfort of use of a kit of parts according to the present invention is substantially enhanced if the external element is mounted on a motorized X-Y table supported in a support structure defining a rim, allowing the external element to be automatically moved with respect to the rim along two directions, X and Y, of the motorized X-Y table, parallel to said rim as a function of the energy received by each of the N photodetectors from the light beam emitted by the light source, until the primary axis, Z1, of the external element is brought coaxially to the secondary axis, Z2, of the implantable medical device. The X-Y table can for example be actuated by means of wires made of a shape memory alloy connected to a source of electric current.

The present invention also concerns a method for aligning an external element with an implantable medical device implanted under the skin of a patient, said external element and implantable medical device being as defined supra. The method comprises the following steps:

(a) Activate the light source of the implantable medical device in order to emit a light beam along the primary axis, Z1, through the skin of the patient;
(b) Position the external element on the skin of the patient at an approximate position of the implantable medical device;
(c) Move the external element on the skin following the indications of the indicator, until the primary axis, Z1, thereof is coaxial to the secondary axis, Z2, of the implantable medical device, thus defining a coaxial position;
(d) Keep the external element at the coaxial position.

If the external element and implantable medical device have an offset configuration, as the external element is kept at the coaxial position in step (d) supra, the external element is rotated about the primary axis, Z1, according to the direction indicated by the pointer (14), until the primary and secondary transmission axes, Y1, Y2, are coaxial.

If the external element is mounted on a X-Y table as discussed supra, the method can comprise the following steps:

(a) Position the rim of the support structure on the skin of the patient at an approximate position of the implantable medical device such that the implantable medical device be located within a perimeter defined by the rim and maintain the support structure at said position,
(b) Allow a processor to drive the X-Y table to move the external element as defined in claim 13(c) into the coaxial position and keep it at said position, with the primary axis, Z1, being coaxial to the secondary axis, Z2, of the implantable medical device.

BRIEF DESCRIPTION OF THE FIGURES

For a fuller understanding of the nature of the present invention, reference is made to the following detailed description taken in conjunction with the accompanying drawings in which.

DETAILED DESCRIPTION OF THE INVENTION

Figure 1:
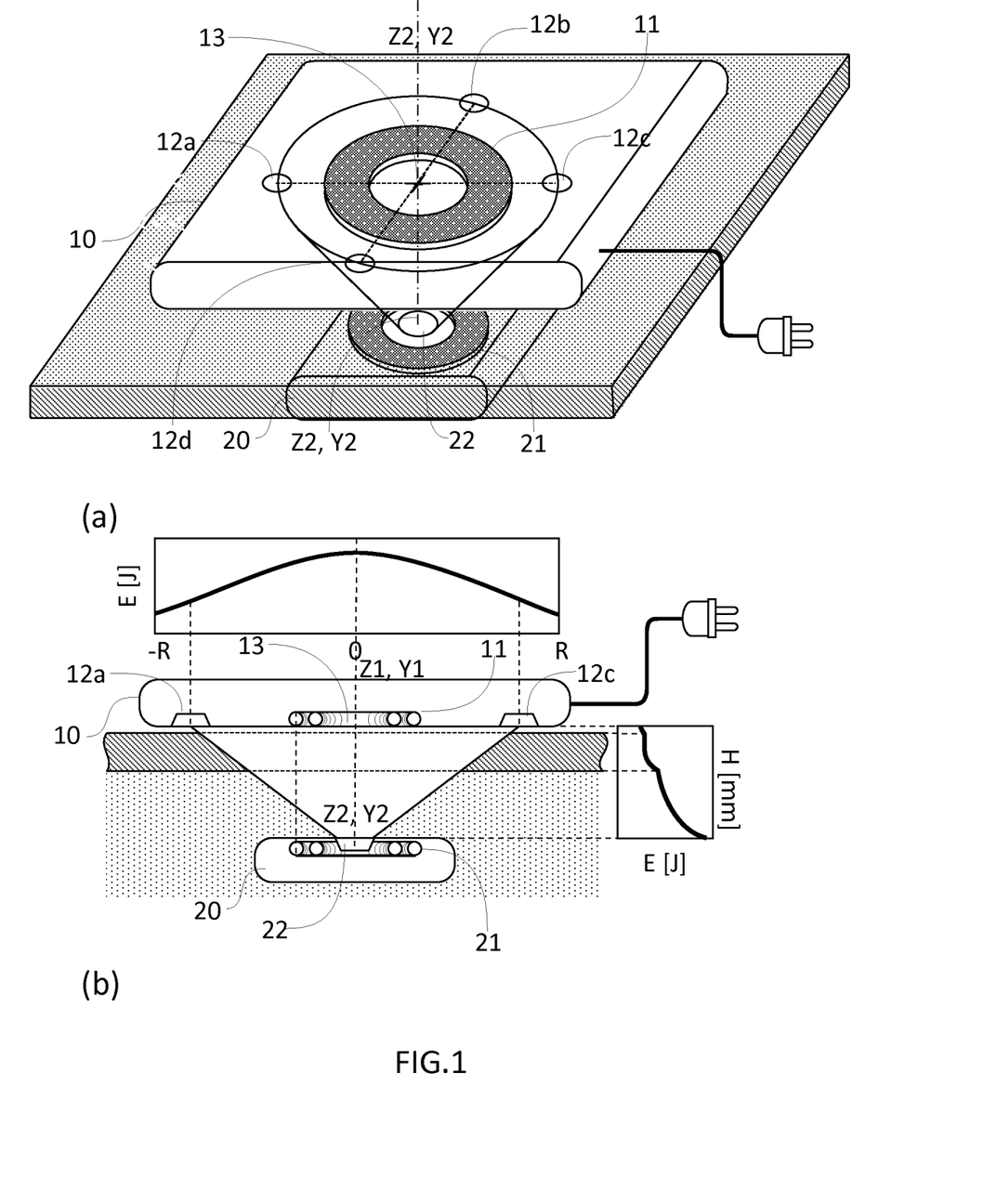
FIG. 1: shows an embodiment of the present invention wherein the external element is a charger comprising a primary coil, and the implanted medical device comprises a secondary coil, which serves to load an internal battery, (a) perspective view, and (b) side view with a graph of the intensity of the light emitted by the light source as a function of the radial distance from the primary axis, Z2.

As illustrated in FIG. 1(a), the present invention comprises (A) an external element (10) comprising an external housing characterized by a primary axis, Z1, and containing an external electronic unit and (B) an implantable medical device (20) (for being) implanted under the skin of a patient and comprising an internal housing characterized by a secondary axis, Z2.

In order to allow the alignment of the external element relative to an implanted medical device, such that the primary and secondary axes, Z1, Z2, are coaxial, the implantable medical device further comprises a light source (22) positioned such as to emit a light beam coaxial to the secondary axis, Z2, and of wavelength and intensity sufficient for being transmitted through the tissues and skin separating the implanted medical device from the exterior when implanted under the skin of a patient. The external element, on the other hand, is provided with:

(a) A number, N>2, of photodetectors (12a-12d) forming a polygon of N edges, normal to the primary axis, Z1, and which centroid (13) belongs to the primary axis, Z1, and
(b) An indicator (4) indicating how the external element is to be displaced over the surface of the skin of a patient in order to position the external element with the primary axis, Z1, being coaxial with the secondary axis, Z2, of the implantable medical device. The indicator is programmed to indicate the required displacement as a function of the energy received by each of the N photodetectors from the light beam emitted by the light source.

Photodetectors are sensors of light or other electromagnetic energy, capable of determining the amount of energy received. In the present invention, photodetectors sensitive to light are preferably used to detect the energy received by each photodetector from the light beam emitted by the light source.

The present invention can be applied to any type of implanted medical device which must cooperate with an external element, which position relative to the implanted medical device is critical for such cooperation to be optimized. For example, the implantable medical device can be a reservoir suitable for dispensing a liquid composition to a body at a controlled rate, and the external element can be a syringe, which needle must be positioned exactly over a filling valve of the implanted reservoir.

Figure 2:
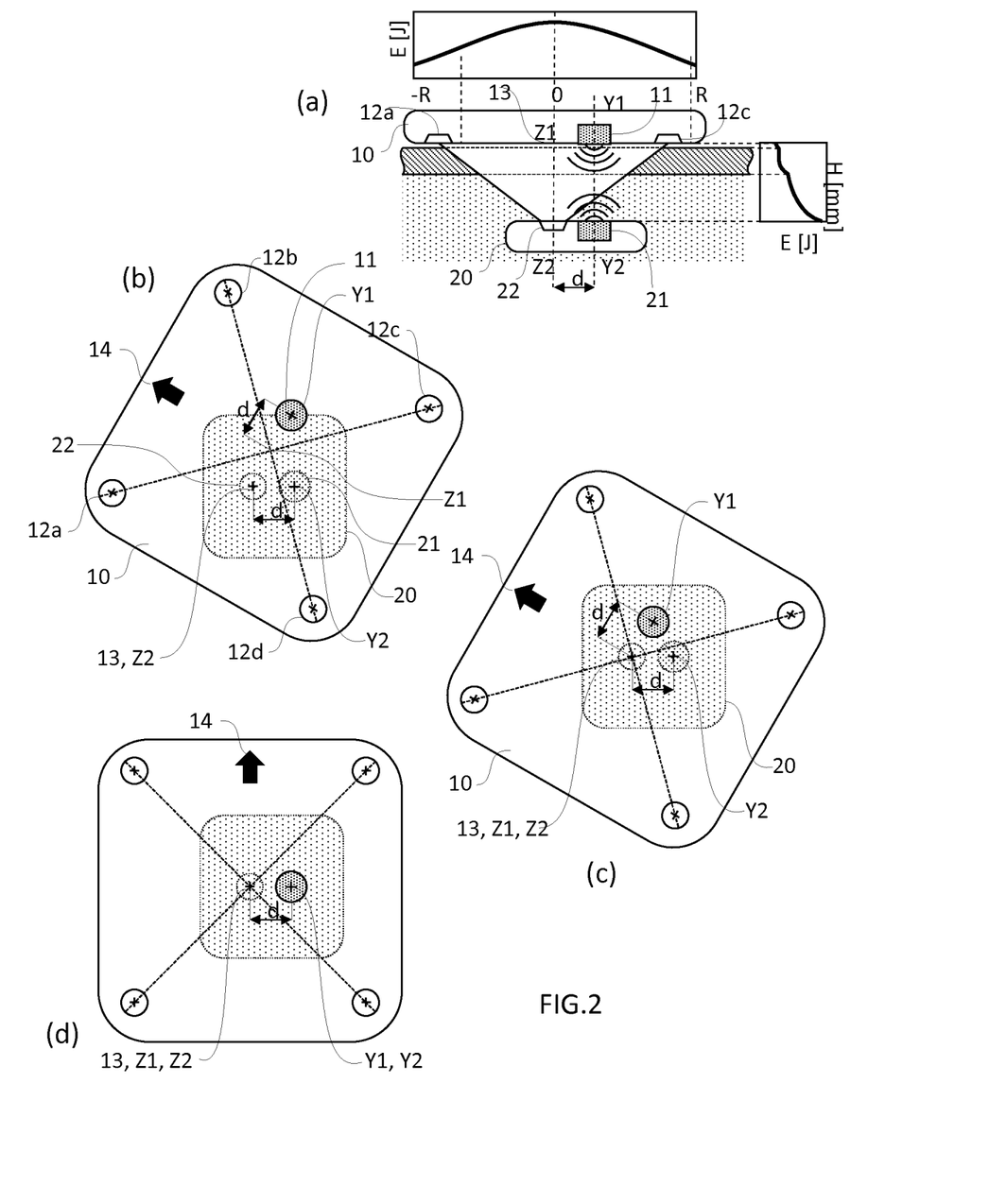
FIG. 2: shows an embodiment wherein the external element and the implanted medical device comprise an emitter/receiver, arranged for emitting/receiving along a transmission axis, Y1,Y2, parallel to and offset from the primary and secondary axes, Z1, Z2; (a) side view, similar to the one of FIG. 1(b), (b) top view with the external element misaligned relative to the implanted medical device, with both Z1 &Z2 and Y1 &Y2 being offset, (c) top view with the external element having Z1 positioned coaxially to Z2, but with Y1 being offset from Y2, and (d) top view with the external element having Z1 and Y1 positioned coaxially to Z2 and Y2, respectively.

In a preferred embodiment illustrated in FIG. 2, the internal housing of the implantable medical device contains an internal electronic unit comprising an internal energy emitter (21) and/or an internal energy receiver (21) defined by a secondary transmission axis, Y2. The external electronic unit of the external element comprises an external energy receiver (11) and/or an external energy emitter (11) defined by a primary transmission axis, Y1. The internal and external electronic units are so configured that when the internal energy emitter and/or internal energy receiver faces the external energy receiver and/or external energy emitter with the secondary transmission axis, Y2, being coaxial to the primary transmission axis, Y1, the secondary axis, Z2, of the implantable medical device is positioned coaxially to the primary axis, Z1. An optimized energy transfer between the internal energy emitter and/or internal energy receiver of the implantable medical device and the external energy receiver and/or external energy emitter of the external element is thus established when the primary and secondary transmission axes, Y1, Y2, are coaxial. The energy being transferred from an emitter to a receiver is preferably transferred in the form of an electromagnetic wave. Typical electromagnetic waves suitable for transferring energy, information or instructions from an emitter to a receiver between an implanted medical device and an external element may include a magnetic field or magnetic link between primary and secondary coils inducing an electrical current in the secondary coil, an optical wave of wavelength comprised between 400 and 1700 nm, preferably between 650 and 1350 nm, a radiowave of frequency comprised between 1 kHz and 2.5 GHz, preferably between 0.1 and 100 MHz, more preferably between 1 and 30 MHz, or a radiowave of frequency comprised between 300 MHz and 2.4 GHz.

As shown in FIG. 1, the implantable medical device and external element may have a coaxial configuration, wherein, The secondary transmission axis, Y2, of the internal energy emitter and/or internal energy receiver of the implantable medical device is coaxial to the secondary axis, Z2, (Y2=Z2), and The primary transmission axis, Y1, of the external energy receiver and/or external energy emitter of the external element is coaxial to the primary axis, Z1, (Y1=Z1).

In a coaxial configuration, it suffices to coaxially align the primary and secondary axes to have an optimal alignment of the emitter/receiver of the implantable medical device and external element such that their respective primary and secondary transmission axes, Y1, Y2, are coaxially aligned too.

Coaxial configurations are possible in the following cases:
if the internal energy emitter/receiver can surround the light source, clearing a central space for accommodating the light source, as illustrated in FIG. 1, wherein a secondary coil (21) surrounds a light source (22),
if the internal energy emitter/receiver is transparent or is located behind the light source (i.e., on the side opposite of the light beam); or
if the light source (22) of the implantable medical device also acts as internal energy emitter for transferring data of the implantable medical device or collected by the implantable medical device in the form of an optical wave.

Because the secondary axis, Z2, necessarily passes by the middle of the light source, it is not always possible to coaxially position Y1 &Z1, on the one hand, and Y2&Z2, on the other hand. The axes Y1 &Z1 and Y2&Z2 must then, respectively, be positioned offset with respect to one another, thus defining an offset configuration. An offset configuration is illustrated in FIG. 2, and is defined as follows:

The secondary transmission axis, Y2, of the internal energy emitter and/or internal energy receiver of the implantable medical device is parallel to and offset from the secondary axis, Z2, by a distance, d, (Y2≠Z2, Y2∥Z2), and The primary transmission axis, Y1, of the external energy receiver and/or external energy emitter of the external element is parallel to and offset from the primary axis, Z1, by the same distance, d, (Y1≠Z1, Y1∥Z1).

Contrary to the coaxial configuration, in an offset configuration system, when the primary axis, Z1, is positioned coaxially to the secondary axis, Z2, the primary transmission axis, Y1, is not necessarily coaxial to the secondary axis, Y2. This is illustrated in FIG. 2 showing an offset configuration system, wherein the primary and secondary transmission axes, Y1 &Y2, are offset by a distance, d, from the corresponding primary and secondary axes, Z1 &Z2. In FIG. 2(b) the external element is positioned approximately over the implantable medical device, with both primary axis, Z1, and primary transmission axis, Y1, being offset with respect to the corresponding secondary axis, Z2, and secondary transmission axis, Y2. Following the indications of the indicator, the external element is moved in FIG. 2(c) such that the primary and secondary axes, Z1 &Z2, are coaxial. It can be seen, however, that the primary and secondary transmission axes, Y1 &Y2, are still offset with respect to one another. As shown in FIG. 2(d), the external element must be rotated about the coaxially aligned primary and secondary axes, Z1 &Z2, in order to bring the primary transmission axis, Y1, coaxially to the secondary transmission axis, Y2, and thus yield an optimal transcutaneous (wireless) transmission of electromagnetic waves between the implanted medical device and the external element.

Once Z1 and Z2 are coaxial, the angle of rotation required to bring Y1 and Y2 coaxially is essential. Implantable medical devices are implanted by a surgeon at a very precise position, and with an accurate orientation. With the knowledge of the location and orientation of the implanted medical device, the external element may comprise a pointer (14) pointing the angular position with respect to the primary axis, Z1, required by the external element in order to bring the primary transmission axis, Y1, coaxially to the secondary transmission axis, Y2, when the primary axis, Z1, and secondary axis, Z2, are coaxial. For example, as illustrated in FIG. 2, the pointer (14) can simply be an arrow or any distinctive sign applied at an appropriate location on a surface of the housing of the external element, indicating the required orientation of the external element, typically up or down, like a compass indicates North. Alternatively, the housing may have a shape indicative of the orientation it must be handled at. For example, hand grips may be arranged such that a natural movement by the user necessarily holds the external element in the right orientation, or an edge of the external element may have a particular geometry and can be used as a reference to, e.g., point up towards the face of the patient. Colour codes or LED's or any means known to a person of ordinary skill in the art, which can be used as reference for the angular orientation of the external element can be used as pointer (14).

Alternatively, the implantable medical device may be provided with a second light source, offset from and emitting a light beam along an internal axis parallel to but offset from Z2, having a different wavelength than the light beam emitted by the light source (22). The external element may be provided with a second set of N>2 photodetectors forming the corners of a polygon centred on an external axis parallel to but offset from Z1, and detecting the light beam emitted by the second light source and not by the light source (22). Filters can be arranged to ensure each set of photodetector detects the energy emitted by the corresponding light source. Once the primary and secondary axes, Z1 and Z2 are coaxially aligned, the second set of photodetectors can be used to indicate how the external element must be rotated in order to coaxially align the internal and external axes. The internal and external axes must be so arranged that once the primary and secondary axes, Z1 &Z2, and the internal and external axes are respectively coaxially aligned; the primary and secondary transmission axes, Y1 &Y2, are also coaxially aligned. This solution is advantageous in that it does not require the knowledge of the exact orientation of the implanted medical device to optimize the positioning of the external element relative the implanted medical device. The second set of photodetectors can be activated together with the photodetectors (12a-12d) or, alternatively, they can be activated sequentially, only after the primary and secondary axes have been coaxially aligned.

It is clear that a coaxial configuration is cheaper, smaller, and simpler to use and, if possible, it is preferable to design a coaxial configuration since, once the primary and secondary axes, Z1, Z2, are coaxial, so are the primary and secondary transmission axes, Y1, Y2, regardless of the angular orientation of the external element.

As discussed supra, the external element comprises an indicator (4) indicating how the external element is to be displaced over the surface of the skin of a patient in order to position the external element with the primary axis, Z1, being coaxial with the secondary axis, Z2, of the implantable medical device. The indicator determines the direction of displacement on the basis of the energy received by each of the N photodetectors from the light beam emitted by the light source. As shown in FIGS. 1(a), 2(a), and 3(a), the intensity of the light beam emitted by the light source decreases radially from the secondary axis, Z2, forming concentric iso-energetic circles centred on the secondary axis, Z2, which radii increase with increasing distance from the light source (22) forming cones. The N photodetectors (12a-12d) being disposed around and centred on the primary axis, Z1, they will all receive the same amount of energy from the light beam only when the primary axis, Z1, is aligned coaxially with the secondary axis, Z2. As shown in FIGS. 3(c) and 4(c), in such configuration all the photodetectors receive the same energy within the optimal deviation, $\varepsilon$, equal to the mean energy, $E_m$, of the energies, received by all the photodetectors. As shown in FIGS. 3(a)&(b) and 4(a)&(b), any deviation of the primary axis, Z1, from coaxiallity with respect to the secondary axis, Z2, will necessarily move one or more photodetectors in a zone of the light beam where the light intensity corresponds to an energy, which is either higher than $E_m+\varepsilon$, or lower than $E_m-\varepsilon$, indicative that the position of the external element is not optimal for cooperation with the implanted medical device.

Based on this principle, in a preferred embodiment, the external element comprises a processor or an electronic logic control circuit configured for carrying out the following steps:

(a) Measure the energy received by each of the photodetectors of the external element from the light source,
(b) Calculate the mean energy, $E_m$, defined as the average of the energies, received by each of the N photodetectors, $E_m = \Sigma E_i/N$, with i=1 to N,
(c) For each photodetector, determine whether the received energy, $E_i$, falls within an optimal range comprised between (Em−$\varepsilon$) and (Em+$\varepsilon$), wherein $\varepsilon$ is a predefined optimal deviation,
(d) If the energy, $E_i$, received by each of the N photodetectors falls within the optimal range, indicate that the external element is optimally positioned with the primary axis, Z1, being coaxial to the secondary axis, Z2, within the optimal deviation,
(e) If the energy, $E_i$, of at least one of the N photodetectors falls out of the optimal range, indicate that the external element is not positioned optimally and optionally indicate the direction the external element must be displaced in order to bring the primary axis, Z1, coaxially to the secondary axis, Z2, of the implantable medical device.

Figure 3:
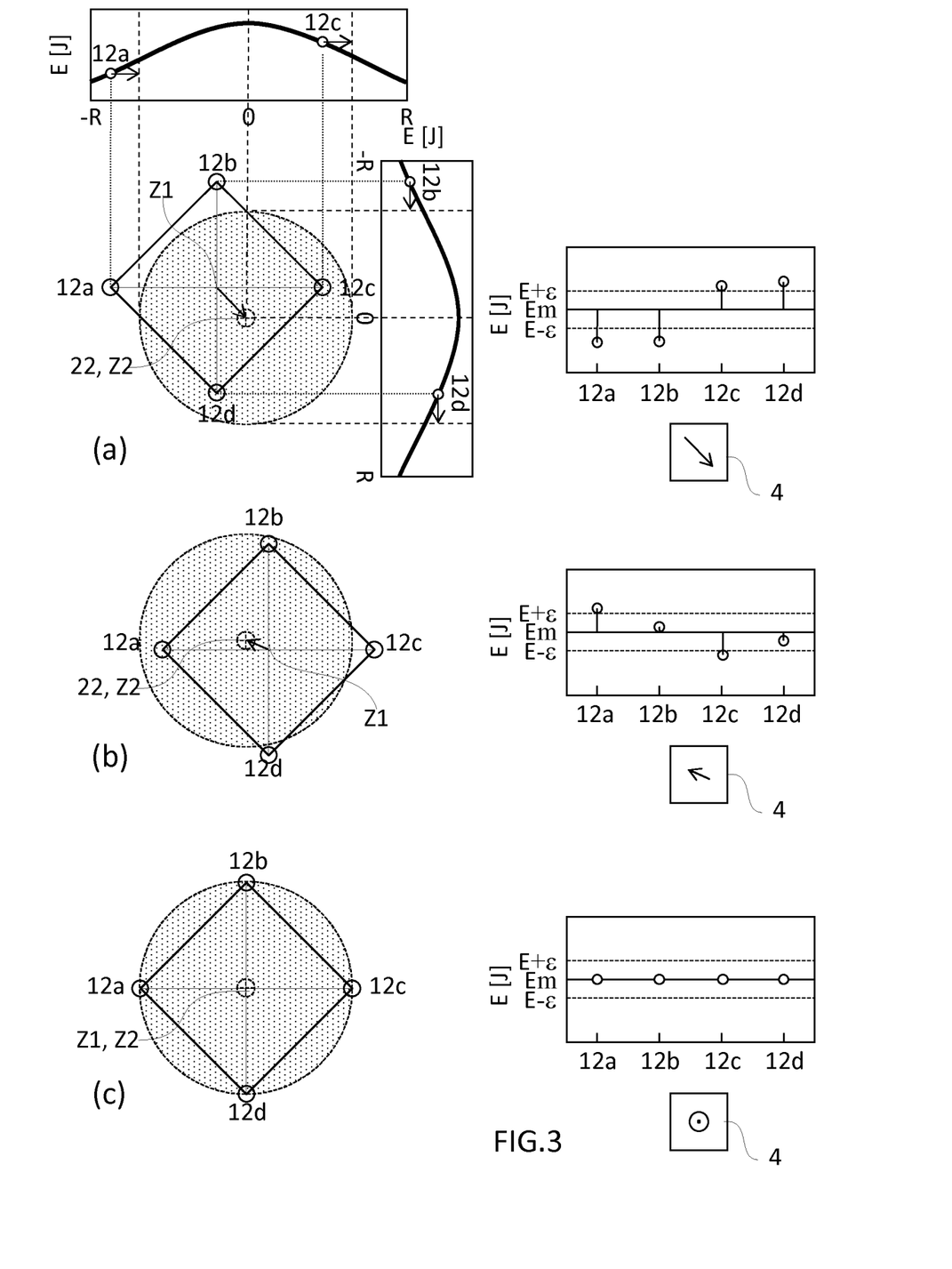
FIG. 3: illustrates the alignment process of the external element relative to the implanted medical device based on the energy received by each photodetector, for a number N=4 photodetectors.
Figure 4:
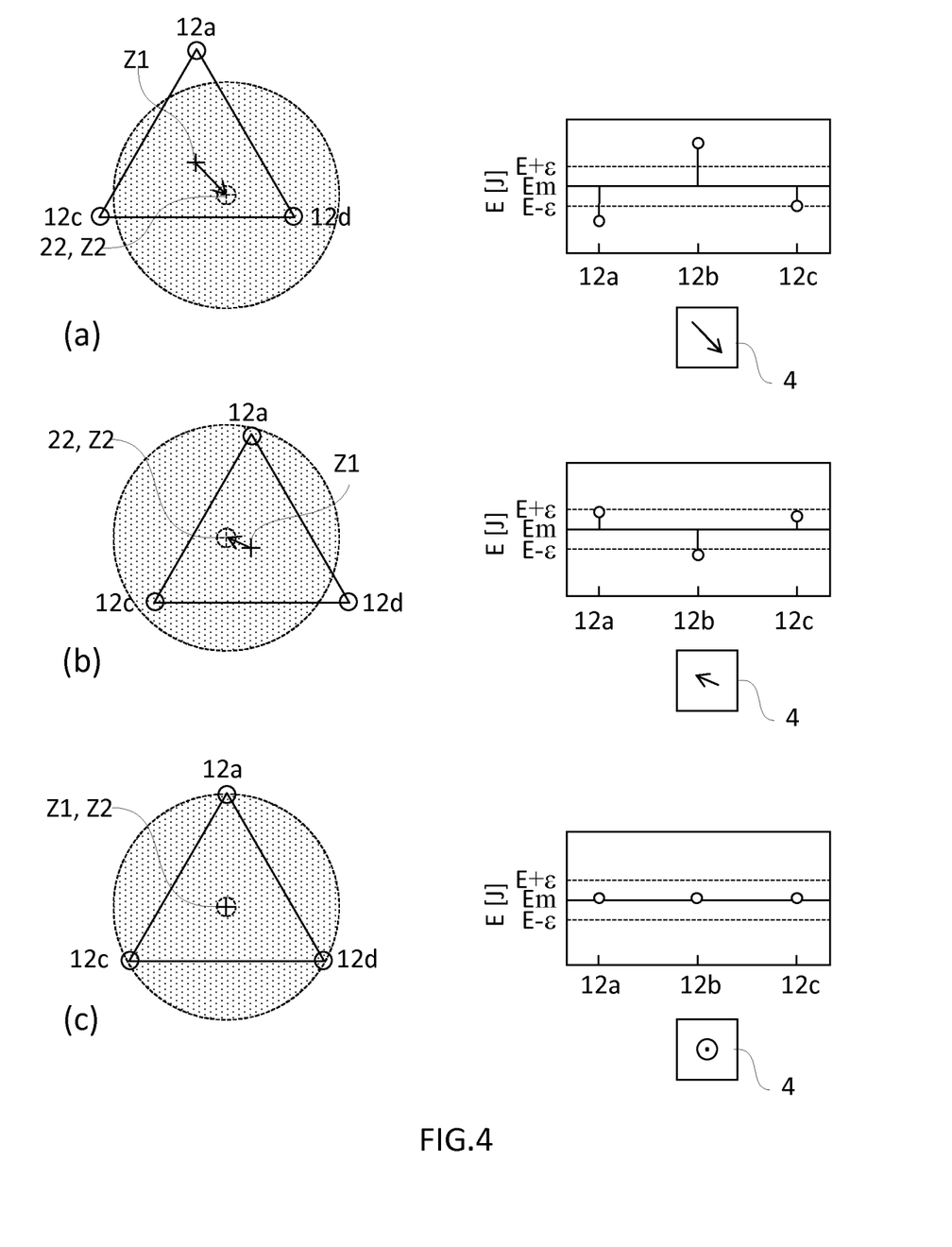
FIG. 4: illustrates the alignment process of the external element relative to the implanted medical device based on the energy received by each photodetector, for a number N=3 photodetectors

The indicator (4) can simply consist of LED's positioned over each photodetector and which are activated only when a given photodetector is in a position wherein it receives an energy, $E_i$, comprised within (or out of) the range $E_m \pm \varepsilon$. The external element must therefore be moved in the direction of the LED's which are off (or on) until they are activated (or deactivated). Alternatively, as shown in FIGS. 3 and 4, an arrow can appear on a display indicating the direction the external element must be moved in. In another embodiment, the indicator can be acoustic, either vocal indicating that the external element must be moved West (or left), South (or down), East (or right), or North (or up) or, alternatively, an acoustic signal which intensity increases or the tone varies as the primary axis, Z1, of the external element is moved closer to coaxiallity with the secondary axis, Z2.

The light source (22) must be positioned at an outer surface of the internal housing or, in case the housing is transparent to the light emitted by the light source, the latter can be housed inside the internal housing. It must be located such that, when the implantable medical device is implanted subcutaneously, the secondary axis, Z2, along which the light beam is emitted by the light source through the skin, is substantially normal to the layers of skin and tissues separating the light source from the outer atmosphere. The wavelength and intensity of the light beam must be sufficient for being transmitted through the tissues and skin. In particular, the light beam preferably has a wavelength comprised between 400 and 1700 nm, preferably between 650 and 1350 nm.

The light source can comprise one or more light units selected among light emitting diodes (LED), laser diodes (LD), vertical cavity laser surface emitting diodes (VCSEL). The several light units can be arranged in a flower pattern, with a central light unit surrounded by 3 to 6 peripheral light units.

A system according to the present invention comprising an implantable medical device and an external element with the alignment solution as discussed above can be implemented in a variety of applications. For example, as illustrated in FIG. 1, the external element can be an electric charger connectable to a source of electric current for feeding in electric current a primary coil made of one or more wires coiled about the primary axis, Z1, thus forming an external emitter (11) of magnetic waves. The internal electronic unit of the implantable medical device can be fed with electric current by a rechargeable battery coupled to a secondary coil made of one or more wires coiled about the secondary axis, Z2, thus forming an internal receiver (21). Because of the annular geometry of the secondary coil, leaving a clearance in the middle to accommodate a light source, such system can be designed with a coaxial configuration, wherein the primary and secondary axes, Z1, Z2, are each coaxial to the corresponding primary and secondary transmission axes, Y1, Y2. When the electric charger is located adjacent to the implantable medical device with the primary axis, Z1, positioned coaxially to the secondary axis, Z2, and when the primary coil is fed with electric current, a magnetic link is formed and the induction of an electric current in the secondary coil is optimized, which serves to recharge the battery of the implantable medical device. An optimal positioning of the external charger with respect to the implanted medical device substantially increases the received power available to recharge the battery and, thus, reduces the charging time of the battery of the implanted medical device, to the benefit and comfort of the patient.

In an alternative application, the external element can be a programming unit and the electromagnetic waves emitted by the external emitter are programming instructions. The internal electronic unit of the implantable medical device can be programmable. Although a coaxial configuration is possible, an offset configuration such as illustrated in FIG. 2 can be easier to design, with the primary and secondary axes, Z1, Z2, are each offset with respect to the corresponding primary and secondary transmission axes, Y1, Y2. When the external energy emitter of the programming unit is positioned adjacent to the internal energy receiver of the programmable implantable medical device with the primary and secondary transmission axes, Y1, Y2, positioned coaxially, the programming instructions emitted by the external energy emitter are received optimally by the internal energy receiver and transmitted to the internal electronic unit.

In yet another application, the external electronic unit of the external element comprises an external receiver allowing the reception of electromagnetic waves propagating in a direction parallel to the primary transmission axis, Y1. The internal electronic unit of the implantable medical device comprises an internal energy emitter configured for emitting electromagnetic waves in a direction parallel to the secondary transmission axis, Y2. When the external energy receiver of the external element is positioned adjacent to the internal energy emitter of the implantable medical device, with the primary and secondary transmission axes, Y1, Y2, positioned coaxially, the electromagnetic wave emitted by the internal energy emitter is received optimally by the external energy receiver. In a preferred embodiment, the electromagnetic wave emitted by the internal energy emitter comprises data of the implantable medical device or data collected by the implantable medical device. In case the electromagnetic energy is an optical wave, the internal energy emitter (21) can advantageously be the light source, thus providing an additional function to the light source and enabling a coaxial configuration.

The external element as discussed supra can be handled by a patient by directly holding the external housing thereof and moving it over the surface of the skin around the approximate position of the implanted medical device. In a preferred embodiment illustrated in FIG. 5, the external element can be mounted on a motorized X-Y table (31) supported in a support structure (30) defining a rim (30r). The external element can thus be automatically moved with respect to the rim along two directions, X and Y, of the motorized X-Y table, parallel to said rim as a function of the energy received by each of the N photodetectors from the light beam emitted by the light source, until the primary axis, Z1, of the external element is brought coaxially to the secondary axis, Z2, of the implantable medical device. The rim of the support structure can simply be laid onto the skin, such that the implantation zone of the implanted medical device is included within a perimeter of the rim, and maintained in that position. The external element is moved by the X-Y table on a plane, (X, Y) parallel to the rim and substantially parallel to the skin of the patient, until it reaches the optimal position with the primary and secondary axes, Z1, Z2, being coaxial. For reasons of comfort for the patient and of torque reduction on the motorized X-Y table, it is preferred that the plane (X, Y) over which the external element can be moved be offset with respect to the rim of the support structure, so that the external element does not, or very lightly, rub against the skin as it is being moved.

Figure 5:
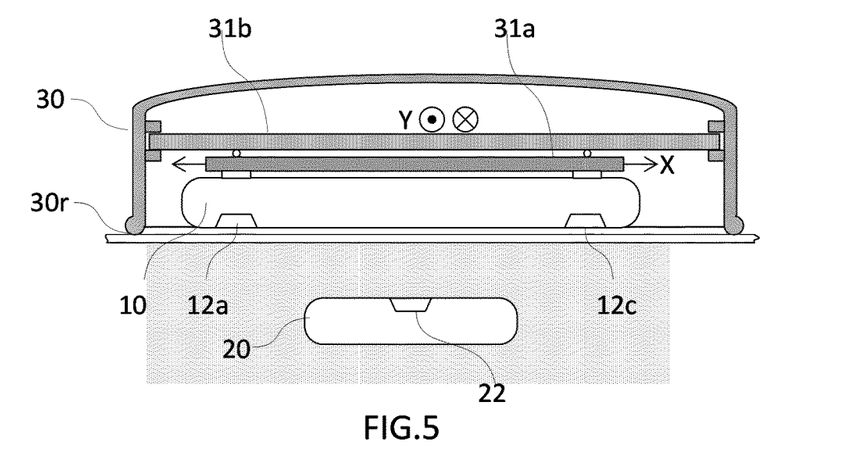
FIG. 5: shows an external element mounted on a motorized X-Y table supported in a support structure defining a rim, allowing the external element to be automatically moved with respect to the rim along two directions, X and Y.

The rim (30r) of the support structure may be provided with padding to increase the feeling of comfort and/or, advantageously, with suction cups to hold the support structure in place without need to holding it to keep it in position. As shown in FIG. 5, the support structure can be bell shaped. Alternatively, it is an open structure. For offset designs, it is preferred that the support structure be provided with a pointer (14) of any type discussed supra. Alternatively, in case an offset configuration system is provided with a second light source and second set of photodetectors as discussed supra, the X-Y table can be rotatably mounted on the support structure so that the external element can be automatically rotated to the required angular position based on the energy received by each photodetector of the second set of photodetectors.

The X-Y table comprises first and second planes (31a, 31b). The first plane (31a) comprises a first moving fixture (33a) which can be moved back and forth along a first direction, X. The second plane (31b) is rigidly coupled to the first moving fixture (33a), and comprises a second moving fixture (33b) which can be moved back and forth along a second direction, Y, normal to X. The external element (10) can be rigidly coupled to the second moving fixture (33b) of the second plane (not shown in FIG. 6), such that it can move back and forth along both directions, X and Y, which define a plane parallel to the rim (30r) and substantially parallel to the skin of the patient covering the implanted medical device.

Motorized X-Y tables comprising a first and second planes (31a, 31b) suitable for being moved along a first and second directions, X and Y, are well known in the art and various models suitable for use in the present invention can be found off the shelves. They usually comprise two electric motors that can move the first and second planes by means of gears, cables, or the like.

Figure 6:
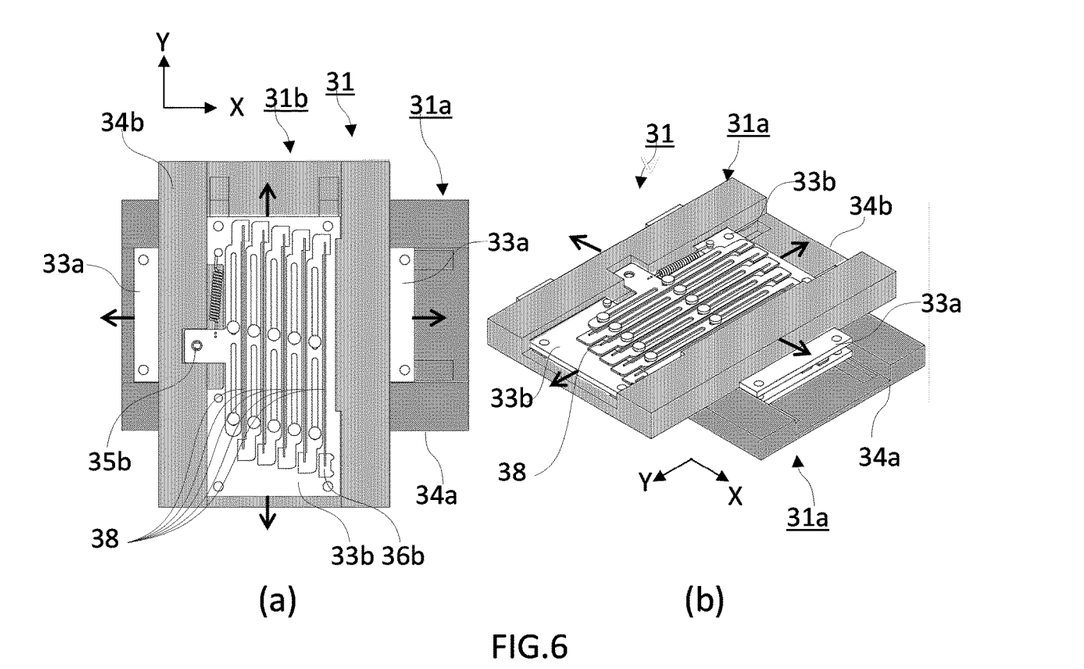
FIG. 6: shows an example of motorized X-Y table comprising shape memory alloy wires.

In a preferred embodiment, the motorized X-Y table (30) is actuated by means of wires (38) made of a shape memory alloys (SMA's) connected to a source of electric current. Such system is substantially more compact than X-Y tables comprising electric motors. An example of SMA's actuated X-Y table available from Miga Motor Company is represented in FIG. 6. It comprises first and second planes (31a, 31b). The first and second planes comprise first and second reference plates (34a, 34b) and first and second moving plates (33a, 33b) which act as the moving fixtures. In each of the first and second planes, one or several SMA wires are stretched and fixed at one end (35b) to the corresponding reference plate (34b) and at the other end (36b) to the corresponding moving plate. When current is circulated through the one or several SMA wires, they shrink and the moving plate moves with respect to the reference plate along the first or second direction, X or Y. By rigidly coupling the first moving plate (33a) to the second reference plate (33b), the second plane (31b) can move back and forth along the first direction X. By rigidly coupling the second reference plate (33b) to the external element (10), the latter can move along both directions X and Y. A spring can be used to assist the return of a moving plate when the SMA wire (38) is cooled and extended to its initial length.

Since the range of the displacement spanned by a moving plate equals the shrinking deformation of a SMA wire when heated, a relatively long wire may be required to achieve such range. One way of using a wire longer than the desired dimensions of the X-Y table is to wind the wire over a number of pulleys arranged between the fixing point (35b) to the reference plate and the fixing point (26b). An alternative solution illustrated in FIG. 6 is to use a number of mobile racks, which are so interlocked that the displacement of one rack by the shrinking of a SMA wire, pushes the rack adjacent thereto, which is further displaced by the shrinking of a second SMA wire, and so on until the fixing point (36b) of the wire to the moving plate.

The present invention also concerns a method for aligning an external element with an implantable medical device implanted under the skin of a patient using an external element and implanted medical device as discussed supra. The method comprises the following steps:

(a) Activate the light source of the implanted medical device in order to emit a light beam along the primary axis, Z1, through the skin of the patient;
(b) Position the external element on the skin of the patient at an approximate position of the implanted medical device;
(c) Move the external element on the skin following the indications of the indicator, until the primary axis, Z1, thereof is coaxial to the secondary axis, Z2, of the implanted medical device, thus defining a coaxial position;
(d) Keep the external element at the coaxial position.

In case the external element is mounted on a X-Y table supported on a support structure as discussed supra, the method comprises the following steps:

(a) Position the rim of the support structure on the skin of the patient at an approximate position of the implanted medical device such that the implantable medical device be located within a perimeter defined by the rim and maintain the support structure at said position,
(b) Allow a processor to drive the X-Y table to move the external element into the coaxial position, with the primary axis, Z1, being coaxial to the secondary axis, Z2, of the implanted medical device.

The present invention offers a solution to the alignment of an external element with respect to an implanted medical device which is efficient, requires little energy, and is very cost-effective. It also permits the automation of the alignment process by mounting the external element on a X-Y table supported in a support structure defining a rim. This option substantially increases the comfort of use as once the rim is in place, the patient needs not worry about neither moving the external element into its optimal position, nor in holding it in place, as the support structure can be fixed in place and the external element finds automatically its optimal position.

| Ref. | Features |
| --- | --- |
| 4 | Indicator |
| 10 | External element |
| 11 | External energy receiver and/or emitter |
| 12a, b, ... | photodetectors |
| 13 | Centroid of the polygon formed by the photodetectors |
| 14 | Pointer |
| 20 | Implantable medical device |
| 21 | Internal energy receiver and/or emitter |
| 22 | Light source |
| 30 | Support structure |
| 30r | Rim of the support structure |
| 31 | X-Y Table |
| 31a | First plane of XY table |
| 31b | Second plane of XY table |
| 33a | First moving fixture/plate |
| 33b | Second moving fixture/plate |
| 34a | First reference plate |
| 34b | Second reference plate |
| 35b | Fixing point of a SMA wire to the reference plate 33b |
| 36b | Fixing point of a SMA wire to the moving plate 34b |
| 38 | SMA wire |
| d | Offset distance between Y1 et Z1, and between Y2 and Z2 |
| Y1 | Primary transmission axis |
| Y2 | Secondary transmission axis |
| Z1 | Primary axis |
| Z2 | Secondary axis |

The invention claimed is:

1. A kit of parts for centering an external element with respect to an implantable medical device, said kit of parts comprising:

(A) an implantable medical device (20) for being implanted under skin of a patient and comprising;
　(a) an internal housing characterized by a secondary axis, (Z2),
　(b) a light source (22) positioned such as to emit a light beam coaxial to the secondary axis, (Z2), and of wavelength and intensity sufficient for being transmitted through tissues and skin separating the implantable medical device from an exterior when implanted under the skin of the patient, and
(B) an external element (10) comprising:
　an external housing characterized by a primary axis (Z1), and containing an external electronic unit, the external element further comprising:
　(a) a number, N>2, of photodetectors (12a-12d) forming a polygon of N edges, normal to the primary axis, (Z1), and which centroid (13) belongs to the primary axis, (Z1), and
　(b) an indicator (4) indicating how the external element is to be displaced over a surface of the skin of the patient in order to position the external element with the primary axis, (Z1), being coaxial with the secondary axis, (Z2), of the implantable medical device,
　characterized in that, the external element further comprises a processor or an electronic logic control circuit configured to:
　　(a) measure energy received by each of the photodetectors of the external element from the light source,
　　(b) calculate a mean energy, Em, defined as an average of the energies, Ei, received by each of the N photodetectors, $Em = \Sigma Ei/N$, with i=1 to N,
　　(c) for each of the photodetectors, determine whether the received energy, Ei, falls within an optimal range comprised between $(Em-\varepsilon)$ and $(Em+\varepsilon)$, wherein ε is a predefined optimal deviation,
　　(d) if the energy, Ei, received by each of the N photodetectors falls within the optimal range, indicate that the external element is optimally positioned with the primary axis (Z1) being coaxial to the secondary axis (Z2) within the optimal deviation, (e) if the energy, Ei, of at least one of the N photodetectors falls out of the optimal range, set the indicator to indicate that the external element is not positioned optimally and to indicate a direction the external element must be displaced in order to bring the primary axis (Z1) coaxially to the secondary axis (Z2) of the implantable medical device.

2. The kit of parts of claim 1, wherein, (a) the internal housing of the implantable medical device contains an internal electronic unit comprising an internal energy emitter (21) or an internal energy receiver (21) defined by a secondary transmission axis, (Y2), and wherein (b) the external electronic unit of the external element comprises an external energy receiver (11) or an external energy emitter (11) defined by a primary transmission axis, (Y1), and wherein when the internal energy emitter or internal energy receiver faces the external energy emitter or external energy receiver with the secondary transmission axis, (Y2), being coaxial to the primary transmission axis, (Y1), the secondary axis, (Z2), of the implantable medical device is positioned coaxially to the primary axis, (Z1), allowing an optimized energy transfer between the internal energy emitter or internal energy receiver of the implantable medical device and the external energy emitter or external energy receiver of the external element.

3. The kit of parts of claim 2, having either:
(a) a coaxial configuration wherein;
  the secondary transmission axis, (Y2), of the internal energy emitter or internal energy receiver of the implantable medical device is coaxial to the secondary axis, (Z2), and
  the primary transmission axis, (Y1), of the external energy receiver or external energy emitter of the external element is coaxial to the primary axis (Z1), (Y1-Z1), or
(b) an offset configuration wherein;
  the secondary transmission axis, (Y2), of the internal energy emitter or internal energy receiver of the implantable medical device is parallel to and offset from the secondary axis, (Z2), by a distance, (d), and
  the primary transmission axis, (Y1), of the external energy receiver, and the external energy emitter of the external element, or a combination thereof is parallel to and offset from the primary axis, (Z1), by said distance, (d), and wherein
  the external element comprises a pointer (14) pointing an angular position with respect to the primary axis, (Z1), required by the external element in order to bring the primary transmission axis, (Y1), coaxially to the secondary transmission axis, (Y2), when the primary axis, (Z1), and the secondary axis, (Z2), are coaxial.

4. The kit of parts of claim 3, wherein:
(A) the external electronic unit of the external element comprises an external receiver allowing the reception of electromagnetic waves propagating in a direction parallel to the primary transmission axis, (Y1), and
(B) the internal electronic unit of the implantable medical device comprises an internal energy emitter configured for emitting electromagnetic waves in a direction parallel to the secondary transmission axis, (Y2), Such that when the external energy receiver of the external element is positioned adjacent to the internal energy emitter of the implantable medical device, with the primary and secondary transmission axes, (Y1, Y2), positioned coaxially, the electromagnetic wave emitted by the internal energy emitter is received optimally by the external energy receiver.

5. The kit of parts of claim 3, wherein:
(A) the external element is a programming unit and electromagnetic waves emitted by the external emitter are programming instructions, and
(B) the internal electronic unit of the implantable medical device is programmable, Such that when the external energy emitter of the programming unit is positioned adjacent to the internal energy receiver of the programmable implantable medical device with the primary and secondary transmission axes, (Y1,Y2), positioned coaxially, the programming instructions emitted by the external energy emitter are received optimally by the internal energy receiver and transmitted to the internal electronic unit.

6. The kit of parts according to claim 3, wherein in the coaxial configuration:
(A) the external element is an electric charger connectable to a source of electric current for feeding in electric current to a primary coil made of one or more wires coiled about the primary axis (Z1), thus forming an external emitter (11) of magnetic waves, and
(B) the internal electronic unit of the implantable medical device is fed with electric current by a rechargeable battery coupled to a secondary coil made of one or more wires coiled about the secondary axis, (Z2), thus forming an internal receiver (21), Such that when the electric charger is located adjacent to the implantable medical device with the primary axis, (Z1), positioned coaxially to the secondary axis, (Z2), and when the primary coil is fed with electric current, a magnetic link is formed and the induction of an electric current in the secondary coil is optimized, which serves to recharge the battery.

7. The kit of parts of claim 2, wherein:
(A) the external element is a programming unit and electromagnetic waves emitted by the external emitter are programming instructions, and
(B) the internal electronic unit of the implantable medical device is programmable, such that when the external energy emitter of the programming unit is positioned adjacent to the internal energy receiver of the programmable implantable medical device with the primary and secondary transmission axes, (Y1,Y2), positioned coaxially, the programming instructions emitted by the external energy emitter are received optimally by the internal energy receiver and transmitted to the internal electronic unit.

8. The kit of parts of claim 2, wherein:
(A) the external electronic unit of the external element comprises an external receiver allowing reception of electromagnetic waves propagating in a direction parallel to the primary transmission axis, (Y1),
(B) the internal electronic unit of the implantable medical device comprises an internal energy emitter configured for emitting electromagnetic waves in a direction parallel to the secondary transmission axis, (Y2), Such that when the external energy receiver of the external element is positioned adjacent to the internal energy emitter of the implantable medical device, with the primary and secondary transmission axes, (Y1, Y2), positioned coaxially, an electromagnetic wave emitted by the internal energy emitter is received optimally by the external energy receiver.

9. The kit of parts of claim 8, wherein the electromagnetic wave emitted by the internal energy emitter comprises data of the implantable medical device or data collected by the implantable medical device.

10. The kit of parts according to claim 9, having a coaxial configuration and wherein the light source (22) of the implantable medical device also acts as internal energy emitter for transferring the data of the implantable medical device or collected by the implantable medical device in the form of an optical wave.

11. The kit of parts according to claim 8, wherein the electromagnetic wave is selected among a magnetic link, an optical wave of wavelength comprised between 400 and 1700 nm, a radiowave of frequency comprised between 1 kHz and 2.5 GHz, or a radiowave of frequency comprised between 300 MHz and 2.4 GHz.

12. The kit of parts according to claim 11, having a coaxial configuration and wherein the light source (22) of the implantable medical device also acts as internal energy emitter for transferring the data of the implantable medical device or collected by the implantable medical device in the form of an optical wave.

13. The kit of parts according to claim 1, wherein the external element is mounted on a motorized X-Y table (30) supported in a support structure (31) defining a rim, allowing the external element to be automatically moved with respect to the rim along two directions (X and Y) of the motorized X-Y table, parallel to said rim as a function of the energy received by each of the N photodetectors from the light beam emitted by the light source, until the primary axis (Z1) of the external element is brought coaxially to the secondary axis (Z2) of the implantable medical device, and wherein the X-Y table is preferably actuated by means of wires (38) made of a shape memory alloy connected to a source of electric current, or with electric motors.

14. A method for aligning an external element with an implantable medical device implanted under skin of a patient, the external element and implantable medical device being as defined in claim 1, said method comprising:
   (a) activating the light source of the implantable medical device in order to emit a light beam along the primary axis, (Z1), through the skin of the patient;
   (b) positioning the external element on the skin of the patient at an approximate position of the implantable medical device;
   (c) moving the external element on the skin following the indications of the indicator, until the primary axis, (Z1), thereof is coaxial to the secondary axis, (Z2), of the implantable medical device, thus defining a coaxial position; and
   (d) keeping the external element at the coaxial position.

15. A method according to claim 14, wherein the external element and implantable medical device have an offset configuration and wherein as the external element is kept at the coaxial position in step (d), the external element is rotated about the primary axis, (Z1), according to the direction indicated by the pointer (14), until the primary and secondary transmission axes, (Y1, Y2), are coaxial.

16. The method of claim 14, wherein the external element and implantable medical device are from a kit of parts according to claim 13, said method comprising:
   (a) positioning the rim of the support structure on the skin of the patient at an approximate position of the implantable medical device such that the implantable medical device be located within a perimeter defined by the rim and maintain the support structure at said position, and
   (b) allowing a processor to drive the X-Y table to move the external element as defined in step (c) of claim 14 into the coaxial position and keep it at said position, with the primary axis, (Z1), being coaxial to the secondary axis, (Z2), of the implantable medical device.

17. The method of claim 14, wherein the external element and implantable medical device are from a kit of parts, said method comprising:
   (a) positioning the rim of the support structure on the skin of the patient at an approximate position of the implantable medical device such that the implantable medical device be located within a perimeter defined by the rim and maintain the support structure at said position, and
   (b) allowing a processor to drive the X-Y table to move the external element as defined in step (c) into the coaxial position and keep it at said position, with the primary axis (Z1) being coaxial to the secondary axis (Z2) of the implantable medical device.

* * * * *